(12) United States Patent
Bottaro et al.

(10) Patent No.: US 6,833,478 B2
(45) Date of Patent: Dec. 21, 2004

(54) N,N-DINITRAMIDE SALTS AS SOLUBILIZING AGENTS FOR BIOLOGICALLY ACTIVE AGENTS

(75) Inventors: Jeffrey C. Bottaro, Mountain View, CA (US); Mark A. Petrie, Cupertino, CA (US); Paul E. Penwell, Menlo Park, CA (US); David C. Bomberger, Belmont, CA (US)

(73) Assignee: SRI International, Menlo Park, CA (US)

( * ) Notice: Subject to any disclaimer, the term of this patent is extended or adjusted under 35 U.S.C. 154(b) by 477 days.

(21) Appl. No.: 09/905,577

(22) Filed: Jul. 13, 2001

(65) **

N,N-DINITRAMIDE SALTS AS SOLUBILIZING AGENTS FOR BIOLOGICALLY ACTIVE AGENTS

TECHNICAL FIELD

This invention relates generally to methods and compositions for increasing the solubility of biologically active agents in lipophilic media. More particularly, the invention relates to the use of N,N-dinitramide salts as solubilizing agents for ionizable biologically active agents, particularly biologically active agents that when ionized are positively charged. The invention finds utility in a variety of fields, including pharmaceuticals and drug delivery, medical imaging and diagnostics, agrochemical manufacture, and dietary supplement formulation.

BACKGROUND

Many hydrophobic compounds are not only poorly soluble or even insoluble in water, but are also insoluble or only slightly soluble in lipophilic media. It is very difficult to manufacture useful products with such compounds because their insolubility limits the ability to chemically transform and/or formulate the compounds in any sort of composition. This is particularly problematic with hydrophobic pharmacologically active agents, which if insoluble in both aqueous and lipophilic media have very low oral bioavailability. Furthermore, for those drugs that are intended to be delivered to the brain, and thus be transported across the "blood-brain barrier" as will be described below, an insufficient amount of the drug penetrates the blood brain barrier and enters the central nervous system.

For treating pathologic processes inside the central nervous system (CNS), therapeutic benefit derives from availability of the agent inside the CNS. Undesired effects can result from effects of the agent anywhere in the body of the treated organism. The blood-brain barrier, regulates the exchange of materials between the bloodstream and the CNS, and may present a formidable barrier to drug transport into the CNS, thus affecting the effective dose of an agent or precluding its use by systemic administration altogether. As physical breach of the meninges is known to be medically undesirable, the inability of a pharmacologic agent to penetrate the blood-brain barrier can preclude its use altogether or limit its use to only life threatening situations.

The physiological basis for the blood-brain barrier are the brain capillaries, which are comprised of a lining of endothelial cells (Goldstein et al. (1986) *Scientific American* 255:74–83 (1986); Pardridge (1986) *Endocrin. Rev.* 7:314–330). The endothelial cells lining the capillaries of the blood-brain barrier are different from those lining capillaries of other tissues. Specifically, they form complex tight junctions, which prevent passage of molecules and ions between cells. The blood-brain barrier is formed by these high-resistance, tight intercellular junctions along with the endothelial cells themselves. The integrated structure forms a continuous wall against the passive movement of many molecules from the blood to the brain. The capillary endothelial cells forming the blood-brain barrier are also different in that they have few pinocytotic vesicles, which allow somewhat unselective transport across the capillary wall in other tissues. Continuous gaps or channels running through the cells, which would allow unrestrained passage of moieties, are also absent in blood-brain barrier capillary lining.

The structure of the blood-brain barrier may be subdivided into two components: the endothelial or capillary barrier and the ependymalbarrier (Banks et al (1991) *Pharm. Res.* 8:1345–1350). The nature of the mechanism of the penetration of substances through the blood-brain barrier has not been fully explained, but many regulators of brain function, such as cytokines, transferrin, enkephalins and endorphins, are believed capable of traversing the blood-brain barrier from the blood vessels into the brain (Raeissi et al (1989) *J. Pharm. Phy.* 41:848–852; Zlokovich et al. (1989) *Peptides* 10:249–254; and Zlokovich, B. (1990) *J. Control. Rel.* 13:185–201). However, many substances that can affect the CNS including adenosine, β-endorphin and synthetic analogs of endogenous peptides and some excitatory and inhibitor amino acids and trophic factors, penetrate the blood-brain barrier poorly or not at all (Houghten et al (1980) *Proc. Natl. Acad. Sci. USA* 77:4588–4591; Levin et al. (1987) *Biochem. Biophys. Res. Commun.* 147:1226–123; Sakane et al. (1989) *Int. J. Pharm.* 57:77–83). Currently, drugs with little or no blood-brain barrier penetration can only be administered by direct CNS infusion or by implantation of controlled-release polymers (see, e.g., U.S. Pat. No. 4,883,666 to Sabel et al.). Thus, many potentially potent drugs are not clinically useful inside the CNS because of inability to cross the blood-brain barrier in amounts capable of yielding therapeutic levels in the CNS at below toxic systemic doses.

Many pharmacologic agents exert desirable therapeutic effects inside the CNS at attainable systemic levels, but can be employed with only limited therapeutic scope because of severe side effects to peripheral organs and/or the peripheral nervous system. Thus, a need generally exists to reduce the side effects of drugs directed to the CNS by reducing side effects on peripheral organs and tissues by increasing the action inside the blood-brain barrier.

One approach has been to alter the permeability of the blood-brain barrier itself. For instance, some osmotic agents administered peripherally, as by intravenous or intramuscular injection, result in the breach of the blood-brain barrier. Further, some drugs acting on the CNS can alter the permeability properties of the blood-brain barrier for other substances. Cholinomimetic arecolines, for example, have been reported to induce alterations of drug penetration through the blood-brain barrier (Saija et al. (1990) *J. Pharm. Pha.* 42:135–138). Other drugs that may be administered to change the blood-brain barrier permeability are disclosed in U.S. Pat. Nos. 5,059,415 and 5,124,146 to Neuwelt. Bradykinin is one specific drug with such effects (see U.S. Pat. No. 5,112,596 to Malfroy-Camine). Another method involves administration of permeabilizer peptides such as A-7 or conformational analogs thereof (see Kozarich et al., International Patent Publication No. WO 92/18529). Tomasz et al. (International Patent Publication No. WO 91/16064) administer parenteral injections of purified cell walls or cell wall fragments of eubacteria such as *Streptococcus pneumoniae* to open the blood-brain barrier, a relatively invasive method.

U.S. Pat. No. 5,260,210 to Rubin et al. discloses a method of increasing the permeability of the blood-brain barrier by administering an agent to reduce or inhibit intracellular cyclic AMP concentrations or to increase cyclic GMP concentrations. One disadvantage of wholesale alteration of blood-brain barrier permeability is the resulting lack of selectivity. Thus, any method of changing the permeability of the blood-brain barrier itself is compromised by the possible entry of unwanted molecules from which the brain is normally protected by the blood-brain barrier. Such methods are thus impracticable due to unpredictable and uncontrollable consequences.

Another approach has been the modification of drug molecules themselves. The properties of the molecule, such as size and $pK_a$, are important to the drug's ability to penetrate the blood-brain barrier. For example, macromolecules, including folded proteins, do not pass the blood-brain barrier at all. One way of modifying a molecule so as to render it capable of traversing the blood brain barrier involves isolating the active moiety of a macromolecule, i.e., that portion of the molecule responsible for the biologically desirable result, and using only that active moiety. Because size is one of the factors affecting ability of a molecule to traverse the blood-brain barrier, reduced size is employed to enhance the kinetics of penetration of the blood-brain barrier, and consequently increase the likelihood that the smaller molecule may traverse the blood-brain barrier in therapeutically significant amounts. Other modifications to macromolecules to enhance passage through the blood-brain barrier include glycating proteins to enhance penetration of the blood-brain barrier, or formation of a prodrug. U.S. Pat. No. 5,260,308 to Podusio et al. teaches glycating proteins, while U.S. Pat. No. 4,933,324 to Shashoua and related International Patent Publication No. WO 89/07938 disclose formation of a prodrug formed from a fatty acid carrier and a neuroactive drug unable to pass through the blood-brain barrier on its own. A similar system is disclosed in WO 89/07938.

One variant of the preceding approach involves linking the desired pharmacoactive compound to a peptide that can facilitate crossing the blood-brain barrier by transcytosis, as described in U.S. Pat. No. 6,030,941 to Summerton et al. In transcytosis, polarized endothelial cells of the capillary, having distinct apical and basolateral membranes, effect traversal of the cell forming a barrier such as the blood-brain barrier. A compound transported by transcytosis is first taken through the apical membrane in the inner capillary wall into a transcytotic vesicle. Transcytotic vesicles typically have an internal pH of about 6.0. The vesicle then transfers the compound to the basolateral membrane of the endothelial cell, on the outer capillary wall. The compound is then expelled from the transcytotic vesicle and across the blood-brain barrier.

Yet another approach is the implantation of controlled release polymers that release the active ingredient from a matrix-system directly into the nervous tissue. However, this approach is invasive and requires surgical intervention for implantation directly into the brain or spinal cord (see Sabel et al., U.S. Pat. No. 4,883,666).

To overcome these limitations, another approach has been tried in which drug carrier systems are used including liposomes, erythrocyte ghosts, antibody-conjugates, and monoclonal antibody conjugates. One of the major problems in targeted drug delivery is the rapid opsonization and uptake of such injected drug carriers by the reticuloendothelial system (RES), especially by macrophages in the liver and spleen. This obstacle may be partially overcome for liposomal and other carrier systems by incorporation of "stealth" lipids, such as phosphatidylinositol, monosialoganglioside.

The aforementioned approaches are rather limited because they are only effective for specific drugs in specific circumstances. Liposomes are probably the least invasive existing method for pharmacological agent delivery across the blood-brain barrier. However, a number of problems are associated with liposomal delivery. For example, liposomes often exhibit severe stability problems and are therefore only of limited clinical use.

Based on these considerations, a long-felt need is apparent for new carrier systems, particularly systems that are capable of transporting molecules that do not penetrate the blood-brain barrier using liposomal delivery. Methods, preparations and drug delivery systems that permit drugs to traverse are likewise needed. Enhancing penetration of the blood-brain barrier should also, ideally, have reduced or minimal peripheral side effects, while at the same time allowing for full therapeutic effect in the nervous system.

There is a specific need for a method and system for transporting lipophilic cations across the blood-brain barrier, as many CNS active agents and other nervous system agents are amine drugs, the term "amine" used loosely to refer to compounds containing a tetravalent nitrogen moiety or a nitrogen moiety capable of being protonated. The present invention is addressed to the aforementioned needs in the art, and provides for effective enhancement of an ionizable (e.g., an amine) compound's lipophilicity and hence solubility in a lipophilic medium, in turn facilitating passage across the blood-brain barrier.

The present method is useful not only in conjunction with delivery of CNS active agents, but also with a host of other pharmacologically active agents, including metal-based drugs.

The invention is not, however, limited to use in drug delivery. The invention finds utility in a host of contexts where there is a need to increase the solubility of a biologically active agent in a lipophilic medium. For example, the invention is useful in conjunction with increasing the lipophilic solubility of medical imaging and diagnostic agents, as well as the lipophilic solubility of "non-pharmacological" nutrients such as dietary supplements, herbal extracts, and the like. In addition, in the agricultural field, many agricultural chemicals (or "agrochemicals"), including insecticides, herbicides, fungicides and other pesticides, have little or no aqueous solubility, and are only slightly soluble in lipophilic solvents.

SUMMARY OF THE INVENTION

Accordingly, in one embodiment, the invention provides a method for enhancing the solubility of an ionizable compound in a lipophilic medium by admixing the ionizable compound with an effective solubility enhancing amount of an N,N-dinitramide salt. The ionizable compound may be in either ionized or un-ionized form prior to admixture, and if in ionized form, in association with an anionic counterion. The ionizable compound, upon ionization, gives rise to a biologically active cationic species that becomes ionically associated with the N,N-dinitramide anion following admixture. The biologically active cationic species may be a pharmacologically active cation.

Preferred ionizable compounds are ionizable pharmacologically active agents, e.g., those which are centrally acting agents such as CNS amines or other nervous system agents, such as: sympathomimetic amines; neuroprotective and neuroregenerative agents, including neurotrophic factors; neuroactive amino acids and peptides; neurotransmitters; agents to treat neurodegenerative disorders; CNS and respiratory stimulants; and drugs that selectively modify CNS function. The ionizable pharmacologically active agent may also be a metal-based drug or a dietary supplement such as a vitamin, a mineral, or another nutritional supplement.

The ionizable compounds may also be medical imaging or diagnostic agents, or an agricultural chemical agent such as a pesticide.

In a related embodiment, the invention provides novel salts formed by reaction of the ionizable compounds with an N,N-dinitramide salt, wherein the salts comprise the biologically active cation of the ionizable compound is in association with N,N-dinitramide anion. The salts have significantly enhanced solubility in lipophilic media relative to that of the ionizable compound.

In a further embodiment, methods of use are provided. One such method is a process for enhancing the penetration of the blood-brain barrier by a pharmacologically active agent, wherein the method involves coadministering the active agent with an N,N-dinitramide salt or coadministering the active agent as an N,N-dinitramide salt.

DETAILED DESCRIPTION OF THE PREFERRED EMBODIMENTS

I. Definitions and Nomenclature

Before the present compounds, compositions and methods are disclosed and described, it is to be understood that this invention is not limited to specific biologically active agents, N,N-dinitramide salts, dosage forms, modes of administration, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a biologically active agent" in a composition or dosage form means that one, two or more biologically active agents can be present in the composition or dosage form, reference to "a pharmaceutically acceptable carrier" includes a single such carrier or a combination of different carriers, and the like.

In this specification and in the claims which follow, reference will be made to a number of terms which shall be defined to have the following meanings:

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 30 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl or lower alkyl.

The term "alkenyl" as used herein refers to a branched or unbranched hydrocarbon group typically although not necessarily containing 2 to about 30 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 30 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. If not otherwise indicated, "hydrocarbyl" indicates unsubstituted hydrocarbyl, substituted hydrocarbyl, heteroatom-containing hydrocarbyl, and substituted heteroatom-containing hydrocarbyl.

By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By the terms "effective amount" or "pharmaceutically effective amount" of an agent as provided herein are meant a nontoxic but sufficient amount of the agent to provide the desired effect.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be administered to an individual along with the active agent(s) without causing any undesirable biological effects or interacting in a deleterious manner with any of the other components of the pharmaceutical composition in which it is contained.

The term "ionizable compound" refers to a compound having at least one ionizable site in its molecular structure. The term "ionizable" does not necessarily mean "ionized," i.e., the ionizable compounds herein may be in either ionized or un-ionized form. Ionization of the ionizable compounds results in formation of a biologically active (e.g., pharmacologically active) cationic species in association with an anionic counterion.

The "solubility" of a compound refers to its solubility in the indicated liquid determined under standard conditions, e.g., at room temperature (typically about 25° C.) and atmospheric pressure, and neutral pH.

The term "hydrophobic" is used to refer to a compound having an octanol:water partition coefficient (at room temperature, generally about 23° C.) of at least about 8:1, preferably at least about 10:1, more preferably 20:1 or higher. The biologically active agents herein are hydrophobic compounds. "Hydrophobic" active agents are sometimes referred to herein as "water insoluble" or "sparingly water soluble," or as having "low aqueous solubility." The term "hydrophilic" refers to a material that is not hydrophobic.

The term "controlled release" is intended to refer to any drug-containing formulation in which release of the drug is not immediate, i.e., with a "controlled release" formulation, oral administration does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). As discussed therein, immediate and nonimmediate release can be defined kinetically by reference to the following equation:

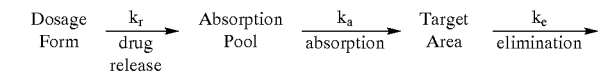

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r << k_a$, such that the rate of release of drug from the dosage form is the rate-limiting step in the delivery of the drug to the target area. The term "controlled release" as used herein includes any nonimmediate release formulation, including but not limited to sustained release, delayed release and pulsatile release formulations.

The term "sustained release" is used in its conventional sense to refer to a drug formulation that provides for gradual release of a drug over an extended period of time, and that preferably, although not necessarily, results in substantially constant blood levels of a drug over an extended time period.

By the term "transdermal" drug delivery is meant delivery by passage of a drug through the skin or mucosal tissue and into the bloodstream. "Transdermal" delivery is also intended to encompass passage through scrotal skin.

The term "topical administration" is used in its conventional sense to mean delivery of a topical drug or pharmacologically active agent to the skin or mucosa.

II. The N,N-Dinitramide Salt

The N,N-dinitramide salts useful as solubilizers herein have the formula $M^{+x}[N(NO_2)_2^-]_x$ wherein M is selected so that it is displaced by the biologically active cationic species upon admixture and/or co-administration of the N,N-dinitramide salt with the ionizable compound, and x is the cationic charge of M. M is a cation selected from the group consisting of a metal ion, an inorganic nitrogen-containing cation, and a cationic derivative of an organic compound having one or more tetravalent nitrogen atoms.

Metallic cations: Suitable metals for the M moiety include the alkali metals Li, Na, K, Rb, and Cs of Group 1 of the Periodic Table of the Elements; the Group 2 alkaline earth metals Ca, Ba, Sr, and Mg; the Group 11 metals Cu, Ag, and Au; the Group 12 metals Zn, Cd, and Hg; the Group 3 metals Al, Sc, Y, Ga, In, and the lanthanides (57–71); the Group 4 metals Ti, Zr, Hf, Ge, and Sn; Group 5 metals V, Nb, and Ta; the Group 6 metals Cr, Mo, and W; the Group 7 metals Mn, Tc, and Re; the Group 8 metals Fe, Ru and Os; and the Group 9 metals Co, Rh and Ir; the Group 10 metals Ni, Pd and Pt. Of the foregoing, Li, Na, K, Be, and Mg are preferred. All references to group numbers in the Periodic Table of the Elements are to the new IUPAC format for numbering elements and groups, as set forth in the *CRC Handbook of Chemistry and Physics*, 81$^{st}$ Edition, Lide, Ed., 2001.

As noted above, M may also be an inorganic nitrogen-containing cation, including, but not necessarily limited to, the ammonium ($NH_4^+$), hydrazinium ($H_2N$—$NH_3^+$), nitronium ($O$=$N$=)$^+$), and nitrosonium ($N$=$O^+$) cations, although the ammonium ion is preferred (in which case the N,N-dinitramide salt is referred to as ammonium dinitramide).

Some cationic derivatives of organic compounds having one or more tetravalent nitrogen atoms and have the formula $R_kH_mN_n^{+q}$, wherein:

n is an integer in the range of 1 to 8;

k is an integer in the range of 1 to 2+n;

q is an integer in the range of 1 to n;

m is equal to n+2+q−k; and each R is $C_1-C_{12}$ hydrocarbyl, typically linear or branched lower alkyl.

Preferred nitrogen-containing cations within the aforementioned group contain 1 or 2 nitrogen atoms. Specific examples of such ions include, but are not limited to, $CH_3NH_3^+$, $(CH_3)_2NH_2^+$, $(CH_3)_3NH^+$, $(CH_3)_4N^+$, $C_2H_5NH_3^+$, $(C_2H_5)_2NH_2^+$, $(C_2H_5)_3NH^+$, $(C_2H_5)_4N^+$, $(C_2H_5)(CH_3)NH_2^+$, $(C_2H_5)(CH_3)_2NH^+$, $(C_2H_5)_2(CH_3)_2N^+$, $(C_3H_7)_4N^+$, $(C_4H_9)_4N^+$, $CH_3N_2H_4^+$, $(CH_3)_2N_2H_3^+$, $(CH_3)_2N_2H_3^+$, $(CH_3)_3N_2H_2^+$, $(CH_3)_4N_2H^+$, and $(CH_3)_5N_2^+$.

Other cationic derivatives of organic compounds that can serve as M+ include guanidinium (a cationic derivative of guanidine), biguanidinium (a cationic derivative of biguanidine), the guanylurea cation $H_2N(NH)CNH_2C(O)NH_2)^+$, ethylenediaminium (a cationic derivative of ethylenediamine), piperazinediium (a cationic derivative of piperazine), monoaminoguanidinium (a cationic derivative of monoaminoguanidine), diaminoguanidinium (a cationic derivative of diaminoguanidine), triaminoguanidinium (a cationic derivative of triaminoguanidine), tetrazolium (a cationic derivative of tetrazole), aminotetrazolium (a cationic derivative of aminotetrazole), amino-ammoniumfurazan (a cationic derivative of diaminofurazan), polyvinylammonium (a cationic derivative of polyvinylammonia), and dicyandiamidium (a cationic derivative of dicyandiamide). See, for example, U.S. Pat. Nos. 5,254,324 to Bottaro et al. and 6,117,255 to Blomquist.

Ammonium dinitramide, or "ADN," is a particularly preferred solubilizing agent. ADN has the chemical formula $NH_4^+(N(NO_2)_2^-)$, and can be obtained from SRI International in Menlo Park, Calif. ADN may also be readily prepared, using the methods disclosed in the art. See, for example, U.S. Pat. Nos. 5,198,204 and 5,254,324 to Bottaro et al. and 5,316,749 and 5,415,852 to Schmitt et al., all assigned to SRI International.

III. The Biologically Active Agent

The ionizable compound herein is a biologically active agent that upon ionization gives rise to a biologically active cationic species in association with an anionic counterion. The ionizable compound that is admixed with the N,N-dinitramide salt will, accordingly, be a biologically active agent in one the following forms:

(1) a salt comprised of a biologically active cationic species (generally a nitrogen-containing cationic species that includes at least one positively charged nitrogen atom) and an anionic counterion; or (2) an electronically neutral compound that:

(a) ionizes upon admixture with the N,N-dinitramide salt to give a biologically active cationic species in ionic association with the N,N-dinitramide anion; and/or (b) becomes protonated in an aqueous medium at physiological pH to give a biologically active cationic species in ionic association with one or more hydroxide counterions.

The biologically active agent may be a pharmacologically active agent or any other compound that has a biological, chemical and/or physical effect on a biological system, i.e., on a living organism. Biologically active agents herein include, by way of example, pharmacologically active agents (e.g., prophylactic and therapeutic pharmaceutical agents), medical imaging and diagnostic agents, dietary supplements, and agricultural chemicals.

One group of biologically active agents of interest herein are cationic species having the formula $NR_4^+$, in association with a negatively charged anion. The R groups may be the same or different, and are independently selected from $C_{1-30}$ hydrocarbyl groups, substituted $C_{1-30}$ hydrocarbyl groups, heteroatom-containing $C_{1-30}$ hydrocarbyl groups, and substituted heteroatom-containing $C_{1-30}$ hydrocarbyl groups, e.g., alkyl, alkenyl, alkynyl, alkoxy, aryl, aralkyl, alkaryl, heteroaryl, and the like.

A. Pharmacologically Active Agents

In one embodiment, then, the biologically active agent is a pharmacologically active agent, generally a hydrophobic active agent. Preferred pharmacologically active agents are centrally acting drugs, particularly CNS active agents and other nervous system agents, including, but not limited to, the following: sympathomimetic amines; neuroprotective and neuroregenerative agents, including neurotrophic factors; neuroactive amino acids and peptides; neurotransmitters; muscarinic receptor agonists and antagonists; anticholinesterases; neuromuscular blocking agents; ganglionic stimulating drugs; agents to treat neurodegenerative disorders such as Alzheimer's disease, Huntington's disease, Parkinson's disease, and amyotrophic lateral sclerosis (ALS); anti-epileptic agents; CNS and respiratory stimulants; and drugs that selectively modify CNS function, including anesthetic agents, analgesic agents, antiemetic agents, antihypertensive agents, cerebral vasodilators, hypnotic agents and sedatives, anxiolytics and tranquilizers, neuroleptic agents, anti-microbial agents, alpha adrenergic receptor antagonists, and appetite suppressants. Some agents, as will be appreciated by those of ordinary skill in the art, are encompassed by two or more of the aforementioned groups.

Examples of these pharmacologically active agents are as follows:

Sympathomimetic amines. Sympathomimetic amines, including the catecholamines, are amine drugs that mimic the actions of drugs that activate the sympathetic nervous system, such as epinephrine and norepinephrine. Sympathomimetic amines thus include albuterol, amphetamine, benzphetamine, colterol, diethylpropion, dopamine, dopamine hydrochloride, dobutamine, ephedrine, epinephrine, epinephrine bitartrate, ethylnorepinephrine, ethylnorepinephrine hydrochloride, fenfluramine, fenoldapam, fenoldopam, fenoldopam mesylate, hydroxyamphetamine, hydroxyamphetamine hydrobromide, ibopamine, isoetharine, isoproterenol, isoproterenol hydrochloride, mephentermine, mephentermine sulfate, metaproterenol, metaraminol, metaraminol bitartrate, methoxamine, methoxamine hydrochloride, midodrine, norepinephrine, norepinephrine bitartrate, phendimetrazine, phenmetrazine, phentermine, phenylephrine, phenylephrine hydrochloride, phenylethylamine, phenylpropanolamine, prenalterol, propylhexedrine, ritodrine, terbutaline, terbutaline sulfate, and tyramine.

Neuroprotective and neuroregenerative agents. These include excitatory amino acid antagonists and neurotrophic factors, e.g., brain derived neurotrophic factor, ciliary neurotrophic factor, and nerve growth factor, neurotrophin(NT) 3 (NT3), NT4 and NT5.

Neuroactive amino acids andpeptides. The primary neuroactive amino acids are γ-aminobutyric acid (GABA), glycine, β-alanine, taurine, and glutamate, and the neuroactive peptides include bradykinin, kallidin, des-$Arg^9$-bradykinin, des-$Arg^{10}$-kallidin, des-$Arg^9$-[$Leu^8$]-bradykinin, [D-$Phe^7$]-bradykinin, HOE 140, neuropeptide Y, enkaphalins and related opioid peptides such as $Met^5$- enkaphalin, Leu⁵-enkephalin, α-, β-and γ-endorphin, α-and β-neo-endorphin, and dynorphin.

Neurotransmitters. The primary neurotransmitters, as will be appreciated by those of ordinary skill in the art, are GABA (γ-aminobutyric acid), glycine, glutamate, acetylcholine, dopamine, epinephrine, 5-hydroxytryptamine, substance P, serotonin, enkaphalins and related opioid peptides as above, and catecholamines.

Muscarinic receptor agonists and antagonists. Muscarinic receptor agonists include, by way of example: choline esters such as acetylcholine, methacholine, carbachol, bethanechol (carbamylmethylcholine), bethanechol chloride; cholinomimetic natural alkaloids and synthetic analogs thereof, including arecoline, pilocarpine, muscarine, McN-A-343, and oxotremorine. Muscarinic receptor antagonists are generally belladonna alkaloids or semisynthetic or synthetic analogs thereof, such as atropine, scopolamine, homatropine, homatropine methylbromide, ipratropium, methantheline, methscopolamine and tiotropium.

Anticholinesterases. As is well known, the function of acetylcholinesterase (AChE) is to terminate the action of acetylcholine at the junctions of various cholinergic nerve endings with their effector organs or postsynaptic sites. See, for example, *Goodman Gilman's The Pharmacological Basis of Therapeutics,* 9th Edition, Jardman et al, Eds. (1996), at Chapter 8. Anticholinesterase agents inhibit the action of ACHE and thus results in the accumulation of acetylcholine at cholinergic receptor cites, stimulating cholinergic receptors throughout the CNS and peripheral nervous system (PNS). Anticholinesterases include, for example, ambenonium, ambenonium chloride, demecarium, demecarium bromide, echothiophate iodide, edrophonium, edrophonium chloride, neostigmine, neostigmine bromide, neostigmine methylsulfate, physostigmine, physostigmine salicylate, pyridostigmine, and pyridostigmine bromide.

Neuromuscular blocking agents and ganglionic blocking drugs. Neuromuscular blocking agents include dicholine esters (e.g., succinylcholine), benzylisoquinolines (d-tubocurarine, atracurium, doxacurium, mivacurium) and pipecuronium, rocuronium, vecuronium), while the primary ganglionic stimulating drugs are hexamethonium, trimethaphan, and mecamylamine.

Agents to treat neurodegenerative diseases. Active agents for treating Alzheimer's disease and Huntington's disease are drugs useful for treating dementias and/or enhancing memory and learning processes. Donezepil, donepezil hydrochloride, physostigmine, physostigmine salicylate, tacrine and tacrine hydrochloride are active agents typically used for treatment of Alzheimer's Disease, while fluoxetine and carbamazepine are used to treat Huntington's Disease. Anti-Parkinsonism drugs useful herein include amantadine, apomorphine, bromocriptine, levodopa (particularly a levodopa/carbidopa combination), pergolide, ropinirole, selegiline, trihexyphenidyl, trihexyphenidyl hydrochloride, and anticholinergic agents. ALS is generally treated with spasmolytic (anti-spastic) agents such as baclofen, diazepam, tizanidine, and dantrolene.

Anti-epileptic agents. Suitable anti-epileptic agents are anti-convulsant (anti-seizure) drugs such as azetazolamide, carbamazepine, clonazepam, clorazepate, ethosuximide, ethotoin, felbamate, gabapentin, lamotrigine, mephenytoin, mephobarbital, phenytoin, phenobarbital, primidone, trimethadione, vigabatrin and the benzodiazepines. Benzodiazepines, as is well known, are useful for a number of indications, including anxiety, insomnia, and nausea.

CNS and respiratory stimulants. CNS and respiratory stimulants also encompass a number of active agents useful herein. These stimulants include, but are not limited to, the following: xanthines such as caffeine and theophylline; amphetamines such as amphetamine, benzphetamine hydrochloride, dextroamphetamine, dextroamphetamine sulfate, levamphetamine, levamphetamine hydrochloride, methamphetamine, and methamphetamine hydrochloride; and miscellaneous stimulants such as methylphenidate, methylphenidate hydrochloride, modafinil, pemoline, sibutramine, and sibutramine hydrochloride.

Drugs that selectively modify CNSfunction. These include, without limitation:

(1) anesthetic agents such as ketamine;

(2) opioid analgesics such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol;

(3) nonopioid analgesics such as apazone, etodolac, diphenpyramide, indomethacine, meclofenamate, mefenamic acid, oxaprozin, phenylbutazone, piroxicam, and tolmetin;

(4) antiemetics such as chlorpromazine, cisapride, domperidone, granisetron, metoclopramide, ondansetron, perphenazine, prochlorperazine, promethazine, thiethylperazine, and triflupromazine;

(5) antihypertensive agents such as apraclonidine, clonidine, guanfacine, and guanabenz;

(6) cerebral vasodilators such as vincamine, naftidrofuryl oxalate, papaverine, and nicotinic acid;

(7) hypnotic agents and sedatives such as clomethiazole, ethinamate, etomidate, glutethimide, meprobamate, methyprylon, zolpidem, and barbiturates (e.g., amobarbital, apropbarbital, butabarbital, butalbital, mephobarbital, methohexital, pentobarbital, phenobarbital, secobarbital, thiopental);

(8) anxiolytics and tranquilizers such as benzodiazepines (e.g., alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, triazolam), buspirone, and droperidol;

(9) neuroleptic agents, including antidepressant drugs, antimanic drugs, and antipsychotic agents, wherein antidepressant drugs include (a) the tricyclic antidepressants such as amoxapine, amitriptyline, clomipramine, desipramine, doxepin, imipramine, maprotiline, nortryptiline, protryptiline, and trimipramine, (b) the serotonin reuptake inhibitors citalopram, fluoxetine, fluvoxamine, paroxetine, sertraline, and venlafaxine, (c) monoamine oxidase inhibitors such as phenelzine, tranylcypromine, and (−)-selegiline, and (d) other, "atypical" antidepressants such as bupropion, nefazodone, and trazodone venlafaxine, and antimanic and antipsychotic agents include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole;

(10) anticholinergic drugs such as atropine, scopolamine and glycopyrrolate;

(11) anti-microbial agents such as (a) tetracycline antibiotics and related compounds (chlortetracycline, oxytetracycline, demeclocycline, methacycline, doxycycline, rolitetracycline), (b) macrolide antibiotics such as erythromycin, clarithromycin, and azithromycin, (c) streptogramin antibiotics such as quinupristin and dalfopristin, (d) beta-lactam antibiotics, including penicillins (e.g., penicillin G, penicillin VK), antistaphylococcal penicillins (e.g., cloxacillin, dicloxacillin, nafcillin, and oxacillin), extended spectrum penicillins (e.g., aminopenicillins such as ampicillin and amoxicillin, and the antipseudomonal penicillins such as carbenicillin), and cephalosporins (e.g., cefadroxil, cefepime, cephalexin, cefazolin, cefoxitin, cefotetan, cefuroxime, cefotaxime, ceftazidime, and ceftriaxone), and carbapenems such as imiprenem, meropenem and aztreonam, (e) aminoglycoside antibiotics such as streptomycin, gentamicin, tobramycin, amikacin, and neomycin, (f) glycopeptide antibiotics such as vancomycin, and teicoplanin;

(g) sulfonamide antibiotics such as sulfacetamide, sulfabenzamide, sulfadiazine, sulfadoxine, sulfamerazine, sulfamethazine, sulfamethizole, and sulfamethoxazole, (h) quinolone antibiotics such as ciprofloxacin, nalidixic acid, and ofloxacin;

(i) anti-mycobacterials such as isoniazid, rifampin, rifabutin, ethambutol, pyrazinamide, ethionamide, aminosalicylic, and cycloserine, (j) systemic antifungal agents such as itraconazole, ketoconazole, fluconazole, and amphotericin B, (k) antiviral agents such as acyclovir, famciclovir, ganciclovir, idoxuridine, sorivudine, trifluridine, valacyclovir, vidarabine, didanosine, stavudine, zalcitabine, zidovudine, amantadine, interferon alpha, ribavirin and rimantadine, and (l) miscellaneous antimicrobial agents such as chloramphenicol, spectinomycin, polymyxin B (colistin), and bacitracin;

(12) alpha adrenergic receptor antagonists such as doxazosin, indoramine, phenoxybenzamine, phentolamine, prazosin, tolazoline, terazosin, trimazosin, and yohimbine; and

(13) appetite suppressants such as amphetamine, dextroamphetamine, dextroamphetamine sulfate, diethylpropion hydrochloride, mazindol, methamphetamine hydrochloride, phentermine, and phentennine hydrochloride.

For certain active agents that are commercially available in the form of an acid addition salt, the commercially available salt form is indicated above along with the free base form of the drug. However, any of the foregoing active agents may be in the form of either the free base (i.e., as an un-ionized, electronically neutral compound) or as any pharmaceutically acceptable acid addition salt thereof, formed with either an inorganic or an organic acid. Suitable inorganic acids include, for example, hydrochloric acid, hydrobromic acid, sulfuric acid, nitric acid, and phosphoric acid, while suitable organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The methodology of the invention may also be used with pharmacologically active agents other than the aforementioned "centrally active agents," and include other nitrogenous drugs as well as metal-based drugs, discussed infra, and nutritional supplements, including vitamins, minerals and other dietary supplements.

The term "vitamin" is used in the conventional sense to refer to trace organic substances that are required in the diet, and includes without limitation, thiamin, riboflavin, nicotinic acid, pantothenic acid, pyridoxine, biotin, folic acid, vitamin $B_{12}$, vitamin A, vitamin D, vitamin E and vitamin K. Also included within the term "vitamin" are the coenzymes thereof, such as thiamine pyrophosphates (TPP), flavin mononucleotide (FMM), flavin adenine dinucleotide (FAD), nicotinamide adenine dinucleotide (NAD), nicotinamide adenine dinucleotide phosphate (NADP), Coenzyme A (CoA), Coenzyme Q (CoQ), pyridoxal phosphate, biocytin, tetrahydrofolic acid, and coenzyme $B_{12}$. The term "vitamin" also includes choline and carnitine. The term "mineral" refers to inorganic substances that are required in the human diet, and includes, without limitation, calcium, magnesium, iron, zinc, selenium, copper, manganese, chromium, molybdenum, etc. The term "dietary supplement" as used herein means a substance that has an appreciable nutritional effect when administered in small amounts.

B. Metal-Containing Biologically Active Agents

Metal-based drugs, as alluded to in the aforementioned section, represent an additional class of compounds with which the present invention is useful. The drug may be any metal-containing drug in which the metal atom, when charged and thus in cationic form, is biologically active. Such drugs include, by way of example: anticancer agents, containing Al, Ga, In, Ti, Ru, Pt, Au, or Sn (a specific example is cisplatin); antimicrobial agents, containing Cu, Zn, Ag, Hg, or Bi (such as silver sulfadiazine); antiarthritic agents, containing Au (such as aurothioglucose, aurothiomalate, and auranofin), antipsychotic agents, such as lithium; antihypertensive agents, containing Fe or Zn; antiviral agents containing, e.g., Li, Pt, Au, W, or Cu; antiulcer drugs containing bismuth; antacid agents containing, e.g., Al, Na, Mg or Ca; radiosensitizing agents for cancer therapy, containing, e.g., Pt or Ru; metalloporphyrins and metallochlorins for photodynamic therapy; insulin mimetics containing, e.g., Cr or V; mineral supplements such as Ca, Mg, Fe, Zn, Se, Cu, Mn, Cr, Mo, K; contrast agents for magnetic resonance imaging containing, e.g., Mn, Gd, Fe; X-ray imaging agents, such as Ba-containing compounds; diagnostic radio-imaging agents, e.g. $^{99m}$Tc, $^{111}$In; β-emitters useful for therapy (e.g., $^{90}$Y, $^{212}$Bi);metalloenzyme mimetics (Mn, Cu, Fe); and radiotherapy agents (e.g. Re, Y, Pb).

C. Agricultural Chemicals

Other suitable biologically active agents with which the present invention may be advantageously employed are agricultural chemicals, e.g., compounds that can be used as agricultural fertilizers, nutrients, plant growth accelerants, plant growth controlling chemicals, insect growth regulators, and pesticides, with the term "pesticides" including, but not limited to, acaricides, avicides, bacteriocides, fungicides, insecticides, larvicides, miticides, molluscicides, nematocides, ovicides, predicides, pupicides, and rodenticides. Common pesticides that are ionizable to give a biologically active cation, and may thus benefit from the method and formulations of the invention, include acylalanines, haloacetanilides, triazole derivatives, pyrethroids, formamidines, and strobilurines.

Examples of specific, representative agricultural chemicals with which the methodology of the invention may be advantageously employed include, but are not limited to, the following:

Atrazine (2-chloro-4-ethylamino-6 isopropylamino-s-triazine);
Simazine (2-chloro-4,6,-bis-(ethylamino)-s-triazine);
Dodine (n-dodecylguanidine acetate);
Thiram (tetramethylthiuram disulfide);
Manazon (s-(4,6-diamino-1,3,5-triazin-2-yl methyl) dimethyl phosphorothiolthionate);
PP 675 (5-butyl-2-dimethylamino-4-hydroxy-6-methyl pyrimidine);
PP 062 (5,6-dimethyl-2-dimethylamino-4 pyrimidinyl dimethylcarbamate);
PP 149 (5-n-butyl-2 ethylamino-4-hydroxy-6 methylpyrimidine);
GS 14260 (4-ethylamino-2-methylthio-6-t-butyl-amino-1,3,5-triazine);
Pyrazon (5-amino-4-chloro-2-phenyl-3-pylidazone);
WL 9385 (2-Azido-4-ethylamino-6-t-butylamino-s-triazine);
Ametryne (2-methylmercapto-4-ethylamino-6-isopropyl-amino-s-triazine);
Prometryne(2-methylmercapto-4,6-bisisopropyl amino-s-triazine);
Benefin (N-butyl-N-ethyl-2,2,2-trifluoro-2,6-dinitro-p-toluidine); and
Nitralin (2,6-dinitro-4-methylsulfonyl-N,N-dipropyl-aniline).

IV. Pharmaceutical Compositions, Dosage Forms and Modes of Administration

Pharmaceutical compositions and dosage forms may contain (1) an N,N-dinitramide salt of a biologically active agent as described in Sections IIIA and IIIB, or (2) an N,N-dinitramide anion and the biologically active agent (wherein the active agent may be either electronically neutral or in the form of a salt). Alternatively, the biologically active agent and the N,N-dinitramide salt may be in separate dosage forms. In the latter case, the active agent and the N,N-dinitramide salt may or may not be administered at the same time. In some cases, it may be advantageous for delivery of drugs across the blood-brain barrier for the N,N-dinitramide salt to be administered on the order of 30 minutes to 2 hours before administration of the active agent.

In any of the aforementioned embodiments, the amount of the N,N-dinitramide salt that is co-administered with the biologically active agent should be an effective solubility enhancing amount, i.e., an amount effective to increase the solubility of the biologically active agent in a lipophilic medium and thereby enhance bioavailability and transport across lipophilic membranes and the blood-brain barrier. The effective solubility enhancing amount of the N,N-dinitramide salt is generally selected to provide a molar ratio of the N,N-dinitramide salt to the ionizable compound (i.e., the biologically active agent, whether in ionized or unionized form) in the range of about $0.5z:1$ to about $5z:1$ wherein z is the charge of the biologically active cationic species. Preferably, the amount is selected to provide a molar ratio of the N,N-dinitramide salt to the active agent in the range of about $1z:1$ to about $2z:1$, and most preferably about $1z:1$ to about $1.5z:1$. Of course, if the active agent is administered in the form of an N,N-dinitramide salt, such that a biologically active cationic species is associated with the dinitramide anion, the ratio of the dinitramide anion to the biologically active cationic species will be approximately $1z:1$ wherein, again, z is the charge of the biologically active cationic species.

The compounds may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of biologically active agent administered will, of course, be dependent on the particular active agent, the condition or disorder being treated, the severity of the condition or disorder, the subject's weight, the mode of administration and other pertinent factors known to the prescribing physician.

Depending on the intended mode of administration, the pharmaceutical compositions may be in the form of solid, semi-solid or liquid dosage forms, such as, for example, tablets, capsules, caplets, liquids, suspensions, emulsions, suppositories, granules, pellets, beads, powders, or the like, preferably in unit dosage form suitable for single administration of a precise dosage.

Oral dosage forms are preferred, and include tablets, capsules, caplets, and nonaqueous solutions, suspensions and or syrups, and may also comprise a plurality of granules, beads, powders or pellets that may or may not be encapsulated. Such dosage forms are prepared using conventional methods known to those in the field of pharmaceutical formulation and are described in the pertinent texts, e.g., in Remington: The Science and Practice of Pharmacy, 20$^{th}$ Edition, Gennaro, A. R., Ed. (Lippincott, Williams and Wilkins, 2000).

Tablets are the preferred oral dosage forms, and may be manufactured using standard tablet processing procedures and equipment. One method for forming tablets herein is by direct compression of a powdered, crystalline or granular composition containing the N,N-dinitramide salt, the biologically active agent, or both, alone or in combination with diluents, binders, lubricants, disintegrants, colorants or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the N,N-dinitramide salt of the biologically active agent (or, in an alternative embodiment, as discussed above, the N,N-dinitramide salt and/or the biologically active agent,), the tablet will generally contain other materials such as binders, diluents, lubricants, disintegrants, fillers, stabilizers, surfactants, coloring agents, and the like. An additional active agent may also be included if desired. Binders are used to impart cohesive qualities to the tablet core, and thus ensure that the core remains intact after compression and prior to coating. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate manufacture of the drug-containing core; examples of suitable lubricants include, for example, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, Nineteenth Edition. (1995) cited supra, which describes materials and methods for preparing encapsulated pharmaceuticals. If the active-agent containing composition is present within the capsule in liquid form, a lipophilic carrier is necessary to dissolve the biologically active agent and/or the N,N-dinitramide salt. The lipophilic carrier must be compatible with all components of the composition, and must be suitable for ingestion.

Suitable lipophilic carriers include, but are not limited to, the following: phospholipids such as phosphorylated diacyl glycerides, and particularly phospholipids selected from the group consisting of diacyl phosphatidylcholines, diacyl phosphatidylethanolamines, diacyl phosphatidylserines, diacyl phosphatidylinositols, diacyl phosphatidylglycerols, diacyl phosphatidic acids, and mixtures thereof; fatty acids such as isovaleric acid, valeric acid, caproic acid, enanthic acid, caprylic acid, pelargonic acid, capric acid, lauric acid, myristic acid, palmitic acid, stearic acid, arachidic acid, behenic acid, lignoceric acid, oleic acid, linoleic acid, linolenic acid, and arachidonic acid; lower fatty acid esters comprising esters of the foregoing fatty acids, wherein the carboxylic acid group of the fatty acid is replaced with an ester moiety —(CO)—OR wherein R is a $C_1$–$C_3$ alkyl moiety optionally substituted with one or two hydroxyl groups; fatty alcohols corresponding to the aforementioned fatty acids, wherein the carboxylic acid group of the fatty acid is replaced by a —$CH_2OH$ group; glycolipids such as cerebroside and gangliosides; and oils, including animal oils such as cod liver oil and, menhaden oil, and vegetable oils such as babassu oil, castor oil, corn oil, cotton seed oil, linseed oil, mustard oil, olive oil, palm oil, palm kernel oil, peanut oil, poppyseed oil, rapeseed oil, safflower oil, sesame oil, soybean oil, sunflower seed oil, tung oil or wheat germ oil.

Solid dosage forms, whether tablets, capsules, caplets, or particulates, may, if desired, be coated so as to provide for delayed release. For example, enteric coatings may be necessary if it is desired to prevent drug release in the upper gastrointestinal tract. Enterically coated dosage forms of the invention may be manufactured using standard coating procedures and equipment. Such procedures are known to those skilled in the art and described in the pertinent texts, e.g., in *Remington*, supra. Generally, after preparation of the solid dosage form, an enteric coating composition is applied using a coating pan, an airless spray technique, fluidized bed coating equipment, or the like. Enteric coating compositions comprise a polymeric material that prevents drug release in the acidic environment of the stomach but dissolve sufficiently in the small intestines to gradually release the active agent therein. Suitable enteric polymers include, but are not limited to, cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, shellac, zein, and acrylic acid polymers and copolymers, preferably formed from acrylic acid, methacrylic acid, methyl acrylate, ethyl acrylate, methyl methacrylate and/or ethyl methacrylate.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Preparations according to this invention for parenteral administration include are sterile nonaqueous solutions, suspensions, or emulsions. Examples of nonaqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteriaretaining filter, by incorporating sterilizing agents into the compositions, by irradiating the compositions, or by heating the compositions. They can also be manufactured using a sterile injectable medium.

Although the present compositions will generally be administered orally or parenterally, preferably using a solid oral dosage form, other modes of administration are suitable as well. For example, administration may be rectal or vaginal, preferably using a suppository that contains, in addition to the active agent and/or the N,N-dinitramide salt, excipients such cocoa butter or a suppository wax. Compositions for nasal or sublingual administration are also prepared with standard excipients well known in the art. The pharmaceutical compositions of the invention may additionally be administered by inhalation. Such compositions may be formulated according to techniques well known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents. Preferred formulations for inhalation are particulate formulations administered using a dry powder inhaler, and aerosol formulations containing a suitable propellant and administered using a pressurized metered dose inhaler.

Topical and transdermal administration are also suitable delivery routes in conjunction with the methodology of the invention. Topical formulations may be in any form suitable for application to the body surface, and may comprise, for example, an ointment, cream, gel, lotion, solution, paste or the like, and/or may be prepared so as to contain liposomes, micelles, and/or microspheres. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation.

The invention may also be used in conjunction with administration through the skin or mucosal tissue using conventional transdermal drug delivery systems, wherein the system is comprised of a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The invention accordingly provides a novel and highly effective means for increasing the solubility of a hydrophobic, cationic compound in a lipophilic medium, and for enhancing the transport of a hydrophobic, cationic pharmacologically active agent across the blood-brain barrier. The invention is useful with a wide variety of biologically active agents, and administration as a pharmacologically active agent is not accompanied by any noticeable side effects. The invention thus represents a significant advance in the fields of drug delivery and neuropharmacology.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. Furthermore, the practice of the present invention will employ, unless otherwise indicated, conventional techniques of drug formulation, which are well within the skill of the art. Such techniques are fully explained in the literature. See *Remington: The Science and Practice of Pharmacy*, cited supra, as well as Goodman & Gilman's *The Pharmacological Basis of Therapeutics*, 9th Ed. (New York: McGraw-Hill, 1996).

All patents, patent applications, patent publications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

Protriptylene hydrochloride (100 mg) was dissolved in 100 ml of water and extracted with 100 ml of toluene. Evaporation of the toluene and careful vacuum drying left a residue of 8 mg of the protriptylene hydrochloride, which had been extracted into the toluene layer.

Execution of the above procedure with 34 mg (approximately one molar equivalent) of ammonium dinitramide added to the water layer resulted in the extraction of 15 mg of protriptylene hydrochloride and dinitramide salts extracted into the toluene layer.

EXAMPLE 2

The case of quinine sulfate required much greater volumes of water, as 1 mmole (782 mg) required 900 ml of water to dissolve. This 900 ml was divided into two 450-ml aliquots; the first was extracted with 100 ml of ethyl acetate, resulting in the isolation of 57 mg of the quinine sulfate from the ethyl acetate layer. Addition of 124 mg (1 molar equivalent) of ammonium dinitramide to the second aliquot, followed by extraction with 100 ml of ethyl acetate resulted in the isolation of 121 mg of an undetermined mixture of quinine sulfate and dinitramide from the ethyl acetate layer. The TLC of this extract in acetone/silica gel showed the highly fluorescent sulfate ($R_f$=0.1) and the non-fluorescent dinitramide ($R_f$=0.75). Evidently, dinitramide ion quenches the fluorescence of protonated quinine.

What is claimed is:

1. A method for increasing the solubility of an ionizable compound in a lipophilic medium, wherein ionization of the compound results in a biologically active cationic species in association with an anionic counterion, the method comprising admixing the ionizable compound with an effective solubility enhancing amount of an N,N-dinitramide salt.

2. The method of claim 1, wherein the ionizable compound is a salt comprised of the biologically active cationic species and an anionic counterion.

3. The method of claim 2, wherein the biologically cationic species is a nitrogen-containing cation containing at least one positively charged nitrogen atom.

4. The method of claim 3, wherein the admixing is carried out under conditions that result in replacement of the anionic counterion with N,N-dinitramide anion.

5. The method of claim 1, wherein the ionizable compound is in electronically neutral form prior to admixture with the N,N-dinitramide salt, but upon admixture with the N,N-dinitramide salt ionizes to form a biologically active cationic species ionically associated with N,N-dinitramide anion.

6. The method of claim 1, wherein the ionizable compound becomes protonated in an aqueous medium at physiological pH to give a biologically active cationic species in association with hydroxide counterions.

7. The method of claim 6, wherein the ionizable compound is a nitrogen-containing compound containing at least one nitrogen atom that becomes protonated and thus positively charged in an aqueous medium at physiological pH.

8. The method of claim 1, wherein the ionizable compound is comprised of a non-ionizable precursor modified so as to contain an ionizable site, wherein ionization of the ionizable site results in the biologically active cationic species.

9. The method of claim 1, wherein the N,N-dinitramide salt has the formula $M^{+x}[N(NO_2)_2^-]_x$ wherein M is selected so that it is displaced by the biologically active cationic species upon admixture of the N,N-dinitramide salt with the ionizable compound, and x is the cationic charge of M.

10. The method of claim 1, wherein the N,N-dinitramide salt has the formula $M^{+x}[N(NO_2)_2^-]_x$ wherein M is a cation selected from the group consisting of a metal ion and a nitrogen-containing ion, and x is the cationic charge of M.

11. The method of claim 10, wherein M is a mono, di, or trivalent metal cation.

12. The method of claim 11, wherein M is selected from the group consisting of Li, Na, K, Rb, Cs, Ca, Ba, Sr, Mg, Cu, Ag, Au, Zn, Cd, Hg, Al, Sc, Y, Ga, In, lanthanide elements (57–71), Ti, Zr, Hf, Ge, Sn, V, Nb, Ta, Cr, Mo, W, Mn, Tc, Re, Fe, Co, Ni, Ru, Rh, Pd, Os, Ir, and Pt.

13. The method of claim 12, wherein M is a metal cation selected from the group consisting of Li, Na, K, Be, and Mg.

14. The method of claim 10, wherein M is a nitrogen-containing cation.

15. The method of claim 14, wherein the nitrogen-containing cation is an inorganic nitrogen-containing cation.

16. The method of claim 15, wherein the inorganic nitrogen-containing cation is selected from the group consisting of ammonium, hydrazinium, nitronium and nitrosonium.

17. The method of claim 16, wherein the inorganic nitrogen-containing cation is ammonium.

18. The method of claim 14, wherein the nitrogen-containing cation is an organic nitrogen-containing cation.

19. The method of claim 18, wherein the organic nitrogen-containing cation is a cationic derivative of an organic compound having one or more tetravalent nitrogen atoms.

20. The method of claim 19, wherein the organic nitrogen-containing cation contains 1 to 8 carbon atoms.

21. The method of claim 20, wherein the nitrogen-containing cation contains 1 or 2 carbon atoms.

22. The method of claim 20, wherein M has the formula $R_kH_mN_n^{+q}$, wherein:

n is an integer in the range of 1 to 8;

k is an integer in the range of 1 to 2+n;

q is an integer in the range of 1 to n;

m is equal to n+2+q−k; and each R is independent selected from the group consisting of $C_1$–$C_{12}$ hydrocarbyl moieties.

23. The method of claim 22, wherein each R is independently selected from the group consisting of linear and branched lower alkyl groups.

24. The method of claim 23, wherein M is selected from the group consisting of $CH_3NH_3^+$, $(CH_3)_2NH_2^+$, $(CH_3)_3NH^+$, $(CH_3)_4N^+$, $C_2H_5NH_3^+$, $(C_2H_5)_2NH_2^+$, $(C_2H_5)_3NH^+$, $(C_2H_5)_4 N^+$, $(C_2H_5)(CH_3)NH_2^+$, $(C_2H_5)(CH_3)_2NH^+$, $(C_2H_5)_2(CH_3)_2N^+$, $(C_3H_7)_4N^+$, $(C_4H_9)_4N^+$, $CH_3N_2H_4^+$, $(CH_3)_2N_2H_3^+$, $(CH_3)_3N_2H_2^+$, $(CH_3)_4N_2H^+$, and $(CH_3)_5N_2^+$.

25. The method of claim 18, wherein the organic nitrogen-containing cation is selected from the group consisting of guanidinium, biguanidinium, guanylurea, ethylenediaminium, piperazinediium, monoaminoguanidinium, diaminoguanidinium, triaminoguanidinium, tetrazolium, aminotetrazolium, amino-ammonium-furazan, polyvinylammonium, and dicyandiamidium.

26. The method of claim 1, wherein the ionizable compound is a pharmacologically active agent, and the biologically active cationic species is a pharmacologically active cationic species.

27. The method of claim 26, wherein the pharmacologically active agent is selected from the group consisting of: sympathomimetic amines; neuroprotective agents; neuroactive amino acids; neuroactive peptides; neurotransmitters; muscarinic receptor agonists and antagonists; anticholinesterases; neuromuscular blocking agents; ganglionic stimulating drugs; agents to treat neurodegenerative disorders; antiepileptic agents; CNS and respiratory stimulants; anesthetic agents; analgesic agents; antiemetic agents; antihypertensive agents; cerebral vasodilators; hypnotic agents and sedatives; anxiolytics and tranquilizers; neuroleptic agents; antimicrobial agents; alpha adrenergic receptor antagonists; and appetite suppressants.

28. The method of claim 27, wherein the pharmacologically active agent is a sympathomimetic amine or a pharmaceutically acceptable acid addition salt thereof.

29. The method of claim 28, wherein the sympathomimetic amine is selected from the group consisting of albuterol, amphetamine, benzphetamine, colterol, diethylpropion, dopamine, dobutamine, ephedrine, epinephrine, ethylnorepinephrine, fenfluramine, fenoldapam, hydroxyamphetamine, ibopamine, isoetharine, isoproterenol, mephentermine, metaproterenol, metaraminol, methoxamine, midodrine, norepinephrine, phendimetrazine, phenmetrazine, phentermine, phenylephrine, phenylethylamine, phenylpropanolamine, prenalterol, propylhexedrine, ritodrine, terbutaline, tyramine, pharmaceutically acceptable acid addition salts thereof, and combinations of any of the foregoing.

30. The method of claim 27, wherein the pharmacologically active agent is a neuroprotective agent.

31. The method of claim 30, wherein the neuroprotective agent is a neurotrophic factor.

32. The method of claim 27, wherein the pharmacologically active agent is a neuroactive amino acid.

33. The method of claim 27, wherein the pharmacologically active agent is a neuroactive peptide.

34. The method of claim 27, wherein the pharmacologically active agent is a muscarinic receptor agonist.

35. The method of claim 27, wherein the pharmacologically active agent is a muscarinic receptor agonist.

36. The method of claim 27, wherein the pharmacologically active agent is an anticholinesterase.

37. The method of claim 27, wherein the pharmacologically active agent is a neuromuscular blocking agent.

38. The method of claim 27, wherein the pharmacologically active agent is a ganglionic blocking drug.

39. The method of claim 27, wherein the pharmacologically active agent is an agent to treat a neurodegenerative disorder.

40. The method of claim 39, wherein the neurodegenerative disorder is Alzheimer's disease and the pharmacologically active agent is selected from the group consisting of donepezil, physostigmine, tacrine, pharmaceutically acceptable acid addition salts thereof, and combinations of any of the foregoing.

41. The method of claim 39, wherein the neurodegenerative disorder is Huntington's disease and the pharmacologically active agent is selected from the group consisting of fluoxetine, carbamazepine, and pharmaceutically acceptable acid addition salts and combinations thereof.

42. The method of claim 39, wherein the neurodegenerative disorder is Parkinson's disease and the pharmacologically active agent is selected from the group consisting of amantadine, apomorphine, bromocriptine, levodopa, pergolide, ropinirole, selegiline, trihexyphenidyl, atropine, scopolamine, glycopyrrolate, pharmaceutically acceptable acid addition salts thereof, and combinations of any of the foregoing.

43. The method of claim 39, wherein the neurodegenerative disorder is amyotrophic lateral sclerosis (ALS) and the pharmacologically active agent is selected from the group consisting of baclofen, diazepam, tizanidine, dantrolene, pharmaceutically acceptable acid addition salts thereof, and combinations of any of the foregoing.

44. The method of claim 27, wherein the pharmacologically active agent is an anti-epileptic agent.

45. The method of claim 27, wherein the pharmacologically active agent is a CNS or respiratory stimulant.

46. The method of claim 27, wherein the pharmacologically active agent is an analgesic agent.

47. The method of claim 46, wherein the analgesic agent is selected from the group consisting of alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, tramadol, apazone, etodolac, diphenpyramide, indomethacin, meclofenamate, mefenamic acid, oxaprozin phenylbutazone, piroxicam, tolmetin, pharmaceutically acceptable acid addition salts thereof, and combinations of any of the foregoing.

48. The method of claim 27, wherein the pharmacologically active agent is a cerebral vasodilator.

49. The method of claim 27, wherein the pharmacologically active agent is a neuroleptic agent.

50. The method of claim 49, wherein the neuroleptic agent is an antidepressant drug selected from the group consisting of tricyclic antidepressants, serotonin reuptake inhibitors and atypical antidepressants.

51. The method of claim 1, wherein the biologically active cationic species is a metal cation, and the ionizable compound is a metal-based drug, an imaging agent, a diagnostic agent, or a mineral supplement.

52. The method of claim 51, wherein the ionizable compound is an agriculturally active chemical compound.

53. The method of claim 52, wherein the agriculturally active chemical compound is a pesticide.

54. The method of claim 53, wherein the pesticide is selected from the group consisting of acaricides, avicides, bacteriocides, fungicides, insecticides, larvicides, miticides molluscicides, nematocides, ovicides, predicides, pupicides, and rodenticides.

55. The method of claim 1, wherein the effective solubility enhancing amount of an N,N-dinitramide salt is selected to provide a molar ratio of the N,N-dinitramide salt to the ionizable compound in the range of about 0.5z:1 to about 5z:1 wherein z is the charge of the biologically active cationic species.

56. The method of claim 55, wherein the molar ratio of the N,N-dinitramide salt to the ionizable compound is in the range of about 1z:1 to about 2z:1.

57. The method of claim 56, wherein the molar ratio of the N,N-dinitramide salt to the ionizable compound is in the range of about 1z:1 to about 1.5z:1.

58. A salt of N,N-dinitramide anion and a biologically active cation.

59. The salt of claim 58, wherein the biologically active cation is selected from the group consisting of pharmacologically active cations, positively charged imaging agents, positively charged diagnostic agents, and cationic pesticides.

60. The salt of claim 59, wherein the biologically active cation is a pharmacologically active cation.

61. The salt of claim 59, wherein the pharmacologically active cation is selected from the group consisting of protonated pharmacologically active agents, pharmacologically active quaternary ammonium cations, and metal cations.

62. A pharmaceutical formulation comprising a salt of N,N-dinitramide anion and a pharmacologically active cation in a pharmaceutically acceptable carrier.

63. The formulation of claim 62, wherein the pharmacologically active cation is selected from the group consisting of protonated pharmacologically active agents, pharmacologically active quaternary ammonium cations, and metal cations.

64. The formulation of claim 63, which is in the form of a tablet.

65. The formulation of claim 63, wherein the pharmaceutical carrier is a lipophilic liquid, and the formulation is in liquid form.

66. The formulation of claim 65, wherein the lipophilic liquid is suitable for oral administration.

67. The formulation of claim 65, wherein the lipophilic liquid is suitable for parenteral administration.

68. A pharmaceutical formulation comprising (a) an ionizable compound that upon ionization gives a pharmacologically active cation, (b) an effective solubility enhancing amount of an N,N-dinitramide salt, and (c) a pharmaceutically acceptable carrier.

69. The formulation of claim 68, wherein the pharmacologically active cation is selected from the group consisting of protonated pharmacologically active agents, pharmacologically active quaternary ammonium cations, and metal cations.

70. The formulation of claim 68, which is in the form of a tablet.

71. The formulation of claim 68, wherein the pharmaceutical carrier is a lipophilic liquid, and the formulation is in liquid form.

72. The formulation of claim 71, wherein the lipophilic liquid is suitable for oral administration.

73. The formulation of claim 71, wherein the lipophilic liquid is suitable for parenteral administration.

74. A biologically active agent delivery system comprised of:

(a) an N,N-dinitramide salt having the formula $M^{+x}[N(NO_2)_2^-]_x$ wherein M is a cation selected from the group consisting of a metal ion and a nitrogen-containing ion, and x is the cationic charge of M; and (b) an ionizable compound, wherein ionization of the compound results in a pharmacologically active cation.

75. The delivery system of claim 74, wherein the N,N-dinitramide salt and ionizable compound are physically segregated.

76. The delivery system of claim 74, wherein the N,N-dinitramide salt and the ionizable compound are contained within a single composition.

* * * * *